United States Patent [19]

Jones

[11] 4,018,896
[45] Apr. 19, 1977

[54] HALO-SUBSTITUTED -2,4,6-TRINITRODIPHENYLAMINES FOR CONTROL OF FOLIAR PHYTOPATHOGENS

[75] Inventor: Reuben G. Jones, Cedar City, Utah

[73] Assignee: Eli Lilly and Company, Indianapolis, Ind.

[22] Filed: Dec. 13, 1974

[21] Appl. No.: 533,042

[52] U.S. Cl. .............................................. 424/330
[51] Int. Cl.² ...................... A01N 9/20; A01N 9/24
[58] Field of Search ................................... 424/330

[56] References Cited

UNITED STATES PATENTS

| 2,158,956 | 5/1939 | Britton et al. ...................... 424/330 |
| 3,719,765 | 3/1973 | Battershell ......................... 424/304 |

FOREIGN PATENTS OR APPLICATIONS

| 2,363,602 | 12/1973 | Germany |
| 721,370 | 1/1972 | South Africa |
| 845,916 | 8/1960 | United Kingdom |

Primary Examiner—Albert T. Meyers
Assistant Examiner—D. W. Robinson
Attorney, Agent, or Firm—Joseph A. Jones; Everet F. Smith

[57] ABSTRACT

A class of 2,4,6-trinitrodiphenylamines having halo substituents on the ring which does not bear nitro groups are active inhibitors of phytopathogens which cause foliar plant diseases.

9 Claims, No Drawings

HALO-SUBSTITUTED -2,4,6-TRINITRODIPHENYLAMINES FOR CONTROL OF FOLIAR PHYTOPATHOGENS

BACKGROUND OF THE INVENTION

This invention belongs to the field of agricultural chemistry, and provides to the art a new method of controlling foliar phytopathogens which cause foliar plant diseases.

A number of publications have disclosed plant-protective compounds which constitute the background of the invention.

For example, British Pat. No. 845,916 discloses that a family of N,N-dialkylanilines, which can bear three nitro groups, are useful as plant fungicides.

Roberts, Ind. Eng. Chem. 34, 497–498 (1942), and Goldsworthy et al., J. Ag. Research 64, 667–678 (1942) discussed phytopathological testing of diphenylamine compounds including 2,4-diaminodiphenylamine and 4-nitrodiphenylamine.

Belgian Pat. No. 780,549 discloses halo-substituted diphenylamines which can bear nitro groups. However, the Belgian patent describes compounds containing at least four halogen atoms, and the phenyl rings of the compounds are alternatively substituted with a variety of groups such as carboxy, sulfonamido, perhalocarbyl, hydrocarbylamino and so forth.

German Offenlegungsschrift No. 2,363,602, published June 27, 1974, describes a group of diphenylamines having diverse substituents, some of which are the same as the substituents of the compounds of this invention.

SUMMARY OF THE INVENTION

A new method of reducing the adverse effects of foliar phytopathogens has been discovered. The method comprises contacting the phytopathogens on the foliage of plants with an effective phytopathogen-inhibiting amount of a compound of the formula

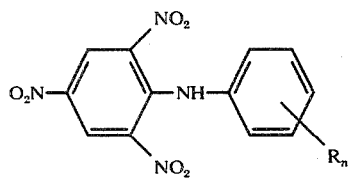

wherein R represents chloro, bromo, fluoro or iodo, and n represents 1–3.

The compounds are particularly useful for the control of foliar phytopathogens of grapes.

DESCRIPTION OF THE PREFERRED EMBODIMENT

All of the compounds named herein are named as trinitrodiphenylamines in the interest of uniformity, even though the rules of nomenclature may call for some compounds to be named otherwise.

The compounds below are typical of the compounds used in the invention. It will be understood that the named compounds do not delineate the scope of the invention, but are named merely to help those of chemical skill to understand the invention.

2′,4′,6′-trifluoro-2,4,6-trinitrodiphenylamine
3′,4′,5′-trichloro-2,4,6-trinitrodiphenylamine
3′,5′-difluoro-2,4,6-trinitrodiphenylamine
3′,4′-difluoro-2,4,6-trinitrodiphenylamine
3′,4′-dibromo-2,4,6-trinitrodiphenylamine
3′,5′-diiodo-2,4,6-trinitrodiphenylamine
3′,4′,5′-tribromo-2,4,6-trinitrodiphenylamine
3′,4′,5′-triiodo-2,4,6-trinitrodiphenylamine
2′,6′-dibromo-2,4,6-trinitrodiphenylamine
2′,4′-diiodo-2,4,6-trinitrodiphenylamine The compounds used in this invention are readily obtained by known methods. In general, the compounds are prepared by the reaction of picryl chloride with an appropriately substituted aniline in an alkanol in the presence of an acid scavenger, such as an inorganic base, an amine or excess of the aniline. The reactions are carried out at room temperature and the yields are economically satisfactory. When a 2′,6′-disubstituted compound is to be made, the reaction goes most effectively in the presence of NaH in a solvent such as dimethylformamide at reduced temperature. The reactions are carried out in anhydrous media and it is best to blanket the reaction vessel with inert gas.

Picryl chloride is a readily obtainable compound. Many of the chloro-substituted anilines which are the other intermediates in the preparation of compounds of this invention are available in the chemical market, and all of them are easily prepared by known methods.

The following preparative examples are presented to assist those skilled in the art in the preparation of the compounds.

EXAMPLE 1

2′-chloro-2,4,6-trinitrodiphenylamine

A 10.2 g. portion of o-chloroaniline was dissolved in 200 ml. of anhydrous denatured ethanol, and 10.0 g. of picryl chloride was added. The mixture was stirred at room temperature under a nitrogen blanket overnight. The mixture was filtered, and the solids were recrystallized from ethanol. Two crops of purified crystals yielded 12.5 g. of 2′-chloro-2,4,6-trinitrodiphenylamine, m.p. 168.5°–170° C. The product was identified by nuclear magnetic resonance analysis and by elemental microanalysis, the results of which follow, calculated for $C_{12}H_7ClN_4O_6$.

|   | Theoretical | Found  |
|---|-------------|--------|
| C | 42.56%      | 42.89% |
| H | 2.08        | 2.15   |
| N | 16.54       | 16.82  |

EXAMPLE 2

2′,6′-dichloro-2,4,6-trinitrodiphenylamine

A 3 g. portion of sodium hydride (57% in mineral oil) was suspended in 50 ml. of dry dimethylformamide at −20° to −10° C. in a nitrogen-blanketed flask. To the suspension was added 10.0 g. of 2,6-dichloroaniline in 75 ml. of dry dimethylformamide over a period of about 20 minutes. The mixture was stirred for about 30 minutes more after the addition. Then, holding the temperature at about −10° C., a solution of 15.3 g. of picryl chloride in 75 ml. of dry dimethylformamide was added over 25 minutes. After the addition, the mixture was stirred for about 90 minutes while the temperature was allowed to rise to about 20° C.

The reaction mixture was then poured over 600 ml. of crushed ice. The resulting black solution was acidified with 3N HCl and was allowed to stand overnight. A precipitate formed, which was filtered from the solution in the morning and recrystallized from ethanol. The yield was 4.26 g. of 2',6'-dichloro-2,4,6-trinitrodiphenylamine, m.p. 182°–184° C., in the form of yellow needle-like crystals. The product was identified by nuclear magnetic resonance ad infrared analyses and by elemental microanalysis, calculated for $C_{12}H_6Cl_2N_4O_6$.

|   | Theoretical | Found |
|---|---|---|
| C | 38.63% | 38.82% |
| H | 1.62 | 1.60 |
| N | 15.02 | 15.30 |
| Cl | 19.00 | 18.91 |

Synthetic methods typified by the above examples are used to produce all of the other compounds useful in this invention. For example, similar methods produce the following exemplary compounds.

EXAMPLE 3

2',4'-dichloro-2,4,6-trinitrodiphenylamine, m.p. 178°–179° C.

EXAMPLE 4

3'-chloro-2,4,6-trinitrodiphenylamine, m.p. 173°–175° C.

EXAMPLE 5

2',3'-dichloro-2,4,6-trinitrodiphenylamine, m.p. 144°–145.5° C.

EXAMPLE 6

2',5'-dichloro-2,4,6-trinitrodiphenylamine, m.p. 146°–148° C.

EXAMPLE 7

3',4'-dichloro-2,4,6-trinitrodiphenylamine, m.p. 180°–181° C.

EXAMPLE 8

2',4',6'-trichloro-2,4,6-trinitrodiphenylamine, m.p. 176°–177° C.

EXAMPLE 9

4'-chloro-2,4,6-trinitrodiphenylamine, m.p. 175.5°–176.5° C.

EXAMPLE 10

2'-fluoro-2,4,6-trinitrodiphenylamine, m.p. 152°–153° C.

EXAMPLE 11

4'-bromo-2,4,6-trinitrodiphenylamine, m.p. 192°–194° C.

EXAMPLE 12

4'-fluoro-2,4,6-trinitrodiphenylamine, m.p. 151°–152° C.

EXAMPLE 13

3'-fluoro-2,4,6-trinitrodiphenylamine, m.p. 133°–134° C.

EXAMPLE 14

2',4'-difluoro-2,4,6-trinitrodiphenylamine, m.p. 136.5°–137° C.

EXAMPLE 15

2',5'-difluoro-2,4,6-trinitrodiphenylamine, m.p. 108°–109° C.

EXAMPLE 16

3'-bromo-2,4,6-trinitrodiphenylamine, m.p. 139°–141° C.

EXAMPLE 17

4'-iodo-2,4,6-trinitrodiphenylamine, m.p. 191°–193° C.

EXAMPLE 18

3'-iodo-2,4,6-trinitrodiphenylamine, m.p. 156°–157.5° C.

The compounds described above have been shown, in a number of in vivo tests, to protect plants from tha adverse effects of foliar phytopathogens. The following examples illustrate the tests employed and the results produced by representative compounds.

Each compound was formulated for testing by dissolving or suspending about 3.5 weight percent of it in 50:50 acetone:ethanol containing about 10 g./100 ml. of a non-ionic surfactant. Pure ethanol was used as the solvent in some downy mildew tests. The solution was then dispersed /in deionized water in a quantity such that the water dispersion contained the various compound concentrations used in the various tests described below. The concentrations are measured in parts per million by weight.

The compound dispersions were applied to the test plants by spraying them with an air atomizer, using sufficient dispersion to wet the plants thoroughly.

Untreated, infected controls and untreated, normal controls were included in each test. The results are reported on a 1–5 rating scale where 1 indicates severe disease and 5 indicates complete control of the disease. A dash in the tables below indicates that the compound was not tested at the rate indicated. In some cases, more than one test was performed against a given phytopathogen, and the results in such cases are reported as averages. Compounds are identified by their example numbers.

TEST 1 downy mildew of grape

Young expanding grape leaves were detached from healthy vines on the day of the test. Leaves were placed individually in plastic petri dishes, bottom side up, on top of an expanded plastic mat. Water was added to each petri dish, and the petiole of each leaf was wrapped with a water-soaked wad of cotton. Each leaf was sprayed with an aqueous dispersion of the compound to be tested.

After the test compound dispersions had dried, the leaves were inoculated by atomizing a conidial suspension of *Plasmopara viticola* (grown on infected leaf tissue) evenly over the leaf surface. The plates were then covered and were stored in a growth room at about 18° C. and 100% relative humidity where they were exposed to 8 hours a day or artificial light. After about a week of storage, all the leaves were observed and the signs of disease were evaluated.

| Example No. | Disease Rating Compound Concentration, ppm. | | | | |
|---|---|---|---|---|---|
| | 800 | 400 | 100 | 50 | 25 |
| 1 | 2 | 1 | — | — | — |
| 2 | 5 | 5 | — | — | — |
| 3 | 5 | 5 | 3 | — | — |
| 4 | 4 | 2 | 3 | — | — |
| 5 | 5 | 5 | 4 | 4 | 4 |
| 6 | 5 | 5 | 3 | — | — |
| 7 | 5 | 5 | 4 | 3 | 2 |
| 8 | 5 | 5 | 5 | 5 | — |
| 9 | 5 | 5 | 3 | 3 | 3 |
| 10 | 4 | 3 | — | — | — |
| 11 | 2 | 3 | 3 | — | — |
| 12 | 2 | 2 | — | — | — |
| 13 | 4 | 4 | — | — | — |
| 14 | — | 4 | 1 | — | — |
| 15 | — | 5 | 4 | — | — |
| 16 | 4 | 3 | — | — | — |
| 17 | 2 | 2 | — | — | — |
| 18 | 3 | 3 | — | — | — |

Tests were also conducted against downy mildew of grape vines growing in field plots. A preferred compound, 2',3'-dichloro-2,4,6-trinitrodiphenylamine, was found to provide 84–92% control of downy mildew. The compound was formulated as an emulsifiable concentrate containing 120 g./ liter, and was applied to the foliage on a 7-day schedule at 600 ppm. concentration. The disease was extremely severe, affecting about 80% of the foliage in untreated control plots. Grape injury caused by the compound was limited to very slight foliage damage.

TEST 2 apple scab of apple

Apple seedlings at the 4–6 leaf stage were sprayed with aqueous dispersions of the test compounds. The following day, the plants were sprayed with a suspension of fresh conidia of *Venturia inaequalis* obtained from infected apple seedlings kept as a source of inoculum. The plants were held for two days in a 20° C. moist chamber to start disease growth and were then transferred to the greenhouse. About two weeks after application of the compounds, the plants were observed and the results were recorded.

| Example No. | Disease Rating Compound Concentration, ppm. | | | |
|---|---|---|---|---|
| | 1200 | 800 | 400 | 200 |
| 3 | — | 1 | — | 1 |
| 4 | — | 1 | — | 1 |
| 5 | 5 | 3 | 1 | 2 |
| 6 | — | 3 | — | 1 |
| 7 | 1 | 5 | 5 | — |
| 9 | 1 | 5 | 5 | — |
| 11 | — | 3 | — | 3 |
| 13 | 5 | 1 | 1 | — |
| 14 | — | — | 1 | — |
| 15 | — | — | 4 | — |

A preferred compound, 2',3'-dichloro-2,4,6-trinitrodiphenylamine, was foliar sprayed on apple trees which were lightly infected by early season apple scab. The infection became very severe as the season progressed. After six periodic applications of an aqueous dispersion of the compound (formulated as an emulsifiable concentrate containing about 120 g. of compound per liter) the disease was controlled to a great extent. When the compound was applied at 600 ppm. concentration, it gave 70–85% control of the disease where about 80% of untreated control foliage was infected. Thus, good control of the disease was provided under extremely severe disease pressure.

TEST 3 cercospora leaf spot of sugar beet

Sugar beet seedlings were transplanted into square plastic pots and allowed to grow for three weeks. Aqueous dispersions containing 400 ppm. of the compounds to be tested were sprayed on the leaf surfaces. After the dispersions dried, but within 24 hours, the plants were inoculated with a conidial suspension of *Cercospora beticola* which had been grown on sugar beet leaf decoction agar. After the plants were held in a moist chamber for 2 days, they were transferred to the greenhouse and observed 2–3 weeks later.

| Example No. | Disease Rating |
|---|---|
| 14 | 1 |
| 15 | 3 |

Another compound, 2',3'-dichloro-2,4,6-trinitrodiphenylamine, was tested against an infection of *C. beticola* on sugar beets growing in the field. Dispersions of the compound were applied three times on a 14-day spray schedule. The compound was formulated as an emulsifiable concentrate containing about 120 g. of compound per liter of concentrate. When the disease control was rated, two weeks after the last treatment, it was found that 67 percent control was obtained from application of 600 ppm. dispersions, and 83 percent control from 1200 ppm. dispersions.

TEST 4 botrytis of grape

Sound grape berries were sterilized by immersion in diluted sodium hypochlorite and thoroughly rinsed. The berries were placed on wire screen shelves in compartmented Pyrex plates. The berries were than flamed and sprayed with test chemical dispersions. The following day, the berries were inoculated by spraying 5 ml. of a conidial suspension of *Botrytis cinerea* over each plate containing 12 berries. The inoculum had been grown on frozen lima bean agar. A small amount of water was added to each plate and a cover was sealed over each plate. After 48 hours at 25° C., the berries were observed and disease ratings recorded.

| Example No. | Disease Rating Compound Concentration, ppm. | | | |
|---|---|---|---|---|
| | 800 | 400 | 200 | 100 |
| 1 | 1 | — | — | — |
| 2 | 1 | — | — | — |
| 3 | 3 | 1 | 1 | 1 |
| 4 | 1 | — | — | — |
| 5 | 2 | 2 | 1 | 1 |
| 6 | 1 | 2 | 1 | 1 |
| 7 | 2 | 1 | 1 | — |
| 9 | 2 | 2 | 1 | — |
| 10 | 1 | 1 | 1 | — |
| 11 | — | 1 | 1 | 1 |
| 12 | 1 | 1 | 1 | — |
| 13 | 2 | 1 | 1 | — |
| 16 | 1 | 1 | 1 | — |
| 17 | 1 | 1 | 1 | — |

-continued

| Example No. | Disease Rating Compound Concentration, ppm. | | | |
|---|---|---|---|---|
| | 800 | 400 | 200 | 100 |
| 18 | 1 | 1 | 1 | — |

The compound of Example 5 was tested against an infection of *Botrytis cinerea* on faba bean (horsebean) growing in field plots. The compound, formulated as an emulsifiable concentrate containing about 120 g./liter, was applied six times on a 7–10 day spray schedule. When the disease control was rated, about two weeks after the last application, an extremely severe infection was found on the control plots. The compound, applied at 600 ppm. concentration, gave 24 percent control of the disease, and gave 68 percent control at 1200 ppm. concentration.

TEST 5 broad spectrum test

Typical compounds were evaluated in a broad spectrum test containing five representative foliar phytopathogens. The individual tests were performed as follows.

late blight of tomato

Four-week-old tomato seedlings were sprayed with aqueous dispersions containing 400 ppm. of the test compounds. The following day, the foliage was inoculated with an aqueous suspension of propagules of *Phytophthora infestans*. The inoculum had been reared on infected wheat seed. The plants were held for two days in a moist chamber to start disease growth, and were then transferred to a greenhouse. The plants were observed and rated for disease control about one week after application of the test compounds.

powdery mildew of bean

The host plants were 10-day-old bean seedlings. After aqueous dispersions containing 400 ppm. of the test compounds had been sprayed on the foliage of the beans and allowed to dry, the plants were placed in the greenhouse and inoculated by storing them under other bean plants which were heavily infected with powdery mildew (*Erysiphe polygoni*). After about 10 days, the plants were observed and the results recorded as usual.

anthracnose of cucumber

Aqueous dispersions containing 400 ppm. of the test compounds were applied to healthy cucumber seedlings grown in sterilized greenhouse soil. The following day, the plants were inoculated with *Colletotrichum lagenarium* conidia as an aqueous suspension. The fungus had been grown on potato dextrose agar in petri dishes. The plants were held in a moist chamber for two days and transferred to the greenhouse. The disease was observed and rated approximately 12 days after application of the test compounds.

rice blast of rice

The test compound dispersions, containing 400 ppm. of the compounds, were applied to healthy rice seedlings growing thickly in plastic pots. The plants were inoculated on the next day with *Piricularia oryzae* (grown on rice polish agar) and the plants were held in a moist chamber for two days. The plants were then held in the greenhouse for 5–7 days and observed.

helminthosporium leaf spot of wheat

Healthy wheat seed was planted in sterile greenhouse soil. When the seedlings were 4–5 inches tall, they were sprayed with 400-ppm. test compound dispersions. The day after treatment, the plants were inoculated with a spore suspension of *Helminthosporium sativum* which had been grown on potato dextrose agar. The plants were placed in a moist growth chamber for 2 days, and then transferred to the greenhouse. About a week after treatment, the plants were observed and the results were recorded.

The following table reports the results of testing representative compounds of this invention in the broad spectrum test against foliar phytopathogens.

| Ex. No. | late blight | powdery mildew bean | anthracnose | rice blast | helminthosporium |
|---|---|---|---|---|---|
| 1 | 1 | 1 | 1 | 1 | 1 |
| 2 | 1 | 1 | 1 | 3 | 1 |
| 3 | 1 | 1 | 3 | 4 | 2 |
| 4 | 1 | 1 | 1 | 1 | 1 |
| 5 | 1 | — | 1 | 4 | 3 |
| 6 | 1 | 1 | 3 | 3 | 3 |
| 7 | 1 | 4 | 1 | 1 | 1 |
| 9 | 1 | 1 | 1 | 1 | 1 |
| 10 | 1 | 1 | 1 | 1 | 1 |
| 11 | 3 | 1 | 1 | 3 | 1 |
| 12 | 1 | 1 | 1 | 1 | 1 |
| 13 | 1 | 1 | 1 | 1 | 1 |
| 14 | 1 | 1 | 3 | 3 | 1 |
| 15 | 1 | 3 | 1 | 4 | 1 |
| 16 | 1 | 1 | 1 | 3 | — |
| 17 | 1 | 1 | 1 | 1 | 1 |
| 18 | 1 | 1 | 1 | 4 | — |

In another informative test, the compound of Example 5, formulated as a 120 g./liter emulsifiable concentrate, was tested against powdery mildew of zinnia in field plots. The compound was applied six times at concentrations of 600 and 1200 ppm. on a 7–10 day spray schedule. By the end of the summer, the control plots were over 60 percent infected with powdery mildew. Under heavy disease pressure, the 600 ppm. treatment gave 70 percent disease control, and the 1200 ppm. treatments gave 85 percent control.

This invention is a method of reducing the adverse effects of foliar phytopathogens which comprise contacting the phytopathogens on the foliage of plants with an effective amount of one of the compounds described above. The preferred compounds, with which the method is most advantageously carried out, are 2',3'-dichloro-2,4,6-trinitrodiphenylamine, 2',4',6'-trichloro-2,4,6-trinitrodiphenylamine, 2',5'-dichloro-2,4,6-trinitrodiphenylamine, 3',4'-dichloro-2,4,6-trinitrodiphenylamine, and 4'-chloro-2,4,6-trinitrodiphenylamine.

The preferred use of the method is in reducing the adverse effects of phytopathogens on the foliage of grapes. The most highly preferred use of the method is in reducing the adverse effects of *Plasmopara viticola*, the causative organism of grape downy mildew.

The method is carried out by applying one of the compounds described above to the foliage where the compound comes into contact with phytopathogens. Those skilled in plant protection will understand that use of the method does not necessarily kill the organisms. Depending on the application rate, the species and vigor of the phytopathogen, and the individual compound chosen, a greater or lesser proportion of the phytopathogen population will be killed and injured. It is well known that reducing the adverse effects of a phytopathogen, even though the disease is not completely eliminated, is of significant benefit to the treated plant. The above data show that application of the method of this invention produces worthwhile reduction of the adverse effects of phytopathogens, as indicated by reduced signs and symptoms of disease.

It is most effective to apply the compound to the foliage before the appearance of signs of infection. Thus, agriculturalists can use the method for the prevention of disease by applying one of the compounds at times when climatic factors are favorable for the growth of phytopathogens. The crop can thereby be protected from the injury which inevitably results from a pathogenic infection. It is also effective, however, to apply the compounds to the foliage after signs or symptoms of infection appear, although, in general, higher application rates of the compounds are necessary after an infection is established. Application of one of the compounds should be started as soon as possible after the first signs of infection appear, for best results.

As is usual in the plant protection art, best results are obtained by applying the compound several times during the growing season at intervals of from one to a few weeks, depending on the weather and severity of the disease.

The methods of formulating the compounds and preparing dispersions of the formulations, and the methods of applying dispersions of the compounds to the plants to be protected, are entirely conventional in the plant protection art. Some explanation of the methods of application will be given merely to assure that those skilled in the art can carry out the invention without undue experimentation.

It is usual in describing foliar applications of plant protectants to measure the application rate by the concentration of the dispersion in which it is applied. The application rate is measured in this way because it is customary to apply a sufficient amount of the dispersion to cover the foliage with a thin film. The amount of dispersion applied is thus dependent on the foliar area of the plants being treated, and the quantity of plant protecting compound is dependent upon its concentration in the dispersion.

Compound concentrations in the range of from about 25 to about 1500 parts of compound per million parts by weight of the dispersion are used in the practice of this invention. Of course, from time to time, higher or lower concentrations will be useful, depending on the severity of the infection and the characteristics of the specific compound in use. The named range, however, encloses the usual optimum concentrations of the compounds.

The dispersions in which the compounds are applied to foliage are most often aqueous suspensions or emulsions prepared from concentrated formulations of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants used for wettable powders.

Adjuvants are frequently used to improve the ability of the aqueous dispersion to coat and adhere to foliage. Such adjuvants as gums, emulsified polybutenes, cationic surfactants and lignin derivatives can often increase the potency of the method in a specific use.

Less frequently, the compounds are applied in the form of dusts. Agricultural chemical dusts typically comprise the compound in a finely powdered form, dispersed in a powdered inert carrier. Most often, the carrier is a powdered clay such as pyrophyllite, bentonite, a volcanic deposit, or montmorillonite. Dusts are usually prepared to contain concentrations of the compound at the highest part of the concentration range, such as 1500 ppm., and may contain even more active ingredient.

Dispersions of the compounds are applied to foliage in the usual manners. Low-pressure sprayers, high-pressure sprayers and low-volume air blast equipment are all effective for the application of water-dispersed compounds of the invention. Dust dispersions are readily applied by means of the usual equipment which blows the dust into intimate contact with the foliage.

I claim:

1. A method of inhibiting fungal pathogens on the foliage of plants which comprises applying to the pathogen or the foliage to be protected an effective fungus-inhibiting amount of a compound of the formula

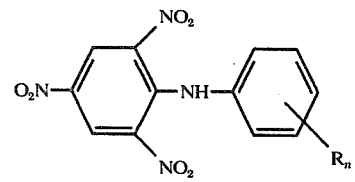

wherein R represents chloro, bromo, fluoro or iodo, and $n$ represents 1–3.

2. A method of claim 1 wherein the amount of the compound is from about 25 to about 1500 ppm.

3. A method of claim 2 wherein the plants are grapes.

4. The method of claim 3 wherein the compound is 2′,3′-dichloro-2,4,6-trinitrodiphenylamine.

5. The method of claim 2 wherein the compound is 2',4',6'-trichloro-2,4,6-trinitrodiphenylamine.

6. The method of claim 2 wherein the compound is 2',5'-dichloro-2,4,6-trinitrodiphenylamine.

7. The method of claim 2 wherein the compound is 3',4'-dichloro-2,4,6-trinitrodiphenylamine.

8. The method of claim 2 wherein the compound is 4'-chloro-2,4,6-trinitrodiphenylamine.

9. The method of claim 2 wherein the compound is 2',3'-dichloro-2,4,6-trinitrodiphenylamine.

* * * * *